United States Patent
Glick et al.

(10) Patent No.: US 7,018,409 B2
(45) Date of Patent: Mar. 28, 2006

(54) ACCOMMODATING INTRAOCULAR LENS ASSEMBLY WITH ASPHERIC OPTIC DESIGN

(75) Inventors: Robert E. Glick, Lake Forest, CA (US); Alan J. Lang, Long Beach, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 141 days.

(21) Appl. No.: 10/243,855

(22) Filed: Sep. 13, 2002

(65) Prior Publication Data

US 2004/0054408 A1    Mar. 18, 2004

(51) Int. Cl.
*A61F 2/16* (2006.01)

(52) U.S. Cl. .................................... 623/6.24; 623/6.37

(58) Field of Classification Search ...... 623/6.17–6.28, 623/6.37, 6.39
See application file for complete search history.

(56) References Cited

U.S. PATENT DOCUMENTS

| | | | | |
|---|---|---|---|---|
| 4,504,982 A | * | 3/1985 | Burk | 623/6.23 |
| 4,580,882 A | * | 4/1986 | Nuchman et al. | 351/161 |
| 4,710,193 A | * | 12/1987 | Volk | 623/6.23 |
| 4,898,461 A | * | 2/1990 | Portney | 351/169 |
| 4,932,966 A | * | 6/1990 | Christie et al. | 623/6.13 |
| 5,173,723 A | * | 12/1992 | Volk | 351/161 |
| 5,408,281 A | * | 4/1995 | Zhang | 351/161 |
| 6,210,005 B1 | * | 4/2001 | Portney | 351/161 |
| 6,231,603 B1 | * | 5/2001 | Lang et al. | 623/6.37 |
| 6,322,213 B1 | * | 11/2001 | Altieri et al. | 351/161 |
| 6,406,494 B1 | * | 6/2002 | Laguette et al. | 623/6.37 |
| 6,457,826 B1 | * | 10/2002 | Lett | 351/161 |
| 6,474,814 B1 | * | 11/2002 | Griffin | 351/161 |
| 6,503,276 B1 | | 1/2003 | Lang et al. | |
| 6,554,859 B1 | | 4/2003 | Lang et al. | |
| 2001/0039451 A1 | * | 11/2001 | Barnett | 623/6.24 |

OTHER PUBLICATIONS

P.U. Fechner, M.D. et al. *Iris-claw lens in phakic eyes to correct hyperopia; preliminary study.* Journal of Cataract Refractive Surgery, vol. 24, Jan. 1998, pp. 48-56.

J.T. Holladay, M.D., et al. *A three-part system for refining intraocular lens power calculations.* Journal of Cataract Refractive Surgery, vol. 14, Jan. 1988, pp. 17-23.

F.K. Jacobi, M.D., et al. *Bilateral implantation of asymmetrical diffractive multifocal intraocular lenses.* Arch Ophthalmology, vol. 117, Jan. 1999, pp. 17-23.

(Continued)

*Primary Examiner*—Corrine McDermott
*Assistant Examiner*—Cheryl Miller
(74) *Attorney, Agent, or Firm*—Advanced Medical Optics, Inc.

(57) ABSTRACT

Intraocular lenses include a lens body sized and adapted for placement in a mammalian eye and having a plurality of different optical powers, and a movement assembly joined to the lens body and adapted to cooperate with the mammalian eye to effect accommodating movement of the lens body in the eye. The lens body has an azonal, aspheric surface, with the correction power of the lens varying continuously and progressively from the optical axis to the periphery of the lens. Such intraocular lenses provide enhanced accommodation relative to the accommodation attainable using a spheric, monofocal IOL adapted for accommodating movement or an aspheric accommodating lens located in a substantially fixed position in an eye.

22 Claims, 2 Drawing Sheets

OTHER PUBLICATIONS

R.B. Mandell, O.D., Ph.D. *Contact lens practice*. Charles C. Thomas Publisher, pp. 1, 211, 212, 385, 403, 404, 491, 492, 792, 819.

J.L. Menezo, M.D., Ph.D., et al. *Endothelial study of iris-claw phakic lens: four year follow-up*. Journal of Cataract Refractive Surgery, vol. 24, Aug. 1998, pp. 1039-1049.

H.M. Shah et al. *The shah bifocal intraocular lens implant*. Six pages.

S. Thornton. *Accommodatin in pseudophakia*, Color Atlas of Lens Implantation, 1991, pp. 159-162.

AMO Specs, Model AC-21B, 1992, 5 pgs. including pp. 179-181.

Final program for the ASCRS Symposium on cataract IOL and refractive surgery, 2 pgs.

Chiron Vision, Nuvita MA20, 1997, 6 pgs.

IOL Technologie Brochure, MF4 The Autofocus Lens, 1995.

CD titled "The Elliptical Accommodative IOL for Cataract Surgery" of videotape shown at ASCRS Symposium on Apr. 10, 1999.

* cited by examiner

ACCOMMODATING INTRAOCULAR LENS ASSEMBLY WITH ASPHERIC OPTIC DESIGN

FIELD OF THE INVENTION

This invention relates to intraocular lenses (IOLs). More particularly, the invention relates to intraocular lenses which provide accommodating movement in the eye.

The human visual system includes the eyes, the extraocular muscles which control eye position within the eye socket, the optic and other nerves that connect the eyes to the brain, and particular areas of the brain that are in neural communication with the eyes. Each eye forms an image upon a vast array of light sensitive photoreceptors of the retina. The cornea is the primary refracting surface which admits light through the anterior part of the outer surface of the eye. The iris contains muscles which alter the size of the entrance port of the eye, or pupil. The crystalline lens has a variable shape within the capsular bag, under the indirect control of the ciliary muscle. Having a refractive index higher than the surrounding media, the crystalline lens gives the eye a variable focal length, allowing accommodation to objects at varying distances from the eye.

Much of the remainder of the eye is filled with fluids and materials under pressure which help the eye maintain its shape. For example, the aqueous humor fills the anterior chamber between the cornea and the iris, and the vitreous humor fills the majority of the volume of the eye in the vitreous chamber behind the lens. The crystalline lens is contained within a third chamber of the eye, the posterior chamber, which is positioned between the anterior and vitreous chambers.

The human eye is susceptible to numerous disorders and diseases, a number of which attack the crystalline lens. For example, cataracts mar vision through cloudy or opaque discoloration of the lens of the eye. Cataracts often result in partial or complete blindness. If this is the case, the crystalline lens can be removed and replaced with an intraocular lens, or IOL.

While restoring vision, conventional IOLs have limited ability for accommodation (i.e., the focusing on near objects). This condition is known as presbyopia. To overcome presbyopia of an IOL, a patient may be prescribed eyeglasses. Alternative attempts in the art to overcome presbyopia focus on providing IOLs with accommodation ability. Accommodation may be accomplished by in a number of ways, including varying the curvature of optic portion of the IOL across its surface, providing zones of differing power, and moving the IOL along its optical axis.

An example of the curvature-changing approach to accommodation is found in U.S. Pat. No. 4,710,193 to Volk. The patent to Volk discloses an IOL having at least one optical surface which is an aspheric surface of revolution having a curvature which varies continuously and regularly from a minimum at its center to a maximum at its periphery.

Examples of the zonal approach to accommodation are disclosed in U.S. Pat. Nos. 4,898,461, 5,225,858, and 6,210,005 to Portney and U.S. Pat. No. 5,847,802 to Menezes. In the Menezes patent, each of the zones has a spherical profile and constant correction, while the IOLs in each of the Portney patents have at least some zones that are aspheric with correction varying continuously from near to far or far to near.

Examples of the axial-movement approach to accommodation are found in U.S. Pat. No. 6,231,603 to Lang et al., issued May 15, 2001 and U.S. Pat. No. 6,176,878 to Gwon et al. The contents of each of these patents are hereby incorporated in their entirety herein. Each of these patents discloses an IOL with a movement assembly that converts radial forces exerted on the capsular bag by the ciliary muscle and/or axial forces exerted on the capsular bag by vitreous fluids into axial movement of the IOL.

The axial-movement approach has met with some success. However, because of space constraints within the eye, axial movement of the lens alone can only vary the corrective power of a lens by about 1–2 diopters. This is insufficient, since the difference in effective power between far and near vision has been estimated to be about +2.5 diopters in the average aphakic patient.

U.S. Pat. No. 6,231,603 B1 to Lang et al, the disclosure of which is hereby incorporated in entirety by reference, represents an attempt to combine the two aforementioned approaches to accommodation. Specifically, the patent to Lang et al shows a zoned, multifocal IOL provided with a movement assembly that cooperates with the ciliary muscle of the eye to extend the IOL away from the retina for near vision, and to retract the IOL toward the retina for distance vision. The accommodation obtained from the axial movement is added to the accommodation from the various zones, resulting in more accommodation than could be obtained from either approach alone.

The accommodating multifocal IOL of Lang et al. overcomes many of the problems associated with prior art accommodating IOLs. Nevertheless, the zoned multifocal design may not be appropriate for all patients. Furthermore, in some cases, over-refractions may occur in some of the zones due to errors in biometric measurements or calculations, or to postoperative changes in intraocular tissue that cause the IOL to shift position.

Accordingly, it would be advantageous to provide IOL assemblies which can achieve full or nearly full accommodation in an average aphakic patient, with a minimum of visual aberrations.

SUMMARY OF THE INVENTION

New accommodating IOLs have been discovered. The present IOLs provide enhanced accommodation with a relatively limited, and readily attainable amount of accommodating movement. The present accommodating IOL assemblies take advantage of one or more of the components and/or features of the eye to provide for the accommodating movement. For example, accommodating movement can be provided by action of the ciliary muscle of the eye and/or of the zonules of the eye and/or by the vitreous pressure within the eye. The correction power of the IOL optic varies across the optical surface to provide further accommodation. The optical surface is configured to provide this variation in correction power without many of the visual side effects associated with prior art multifocal lenses.

In one embodiment, the optical surface is completely aspheric and azonal; that is, rather than having a plurality of distinct regions, the optical surface has a curvature that varies continuously and progressively over the entire optical surface so that the vision correction also varies continuously and progressively.

In still another embodiment, a spherical portion may be combined with an aspheric portion to limit the portion of the optic with variable power. For instance, progressively varying power may be provided along an aspheric peripheral portion of the optical surface, while the center of the lens may be spherical to provide constant add power. Alternatively, the center may be aspheric and a peripheral portion may be spheric.

The movement assembly preferably is adapted to cooperate with the ciliary muscle and/or the zonules of the mammalian eye and/or with the vitreous pressure in the eye to effect accommodating movement of the lens body in the eye. More preferably, the movement assembly is adapted to cooperate with the ciliary muscle and/or zonules of the mammalian eye and/or with the vitreous pressure in the eye to move the lens body toward a first position relative to the retina of the eye, for example, when the ciliary muscle is relaxed, and toward a different second position, for example, when the ciliary muscle is constricted or contracted. The first position of the lens body preferably enhances far vision whereas the second position of the lens body preferably enhances near vision.

In one embodiment, the movement assembly comprises a flexible member that circumscribes the lens body and maintains the lens body in an anteriorly spaced position relative to the posterior wall of the capsular bag of a patient's eye. Preferably, the flexible member is integrally coupled to the lens body via a reduced thickness portion that serves essentially as a hinge facilitating axial movement of the lens body.

Any feature or combination of features described herein is included within the scope of the present invention provided that the features of any such combination are not mutually inconsistent.

Additional aspects and advantages of the present invention are set forth in the following description and claims, particularly when considered in conjunction with the accompanying drawings in which like parts bear like reference numerals.

DETAILED DESCRIPTION OF THE DRAWINGS

Figure 1:
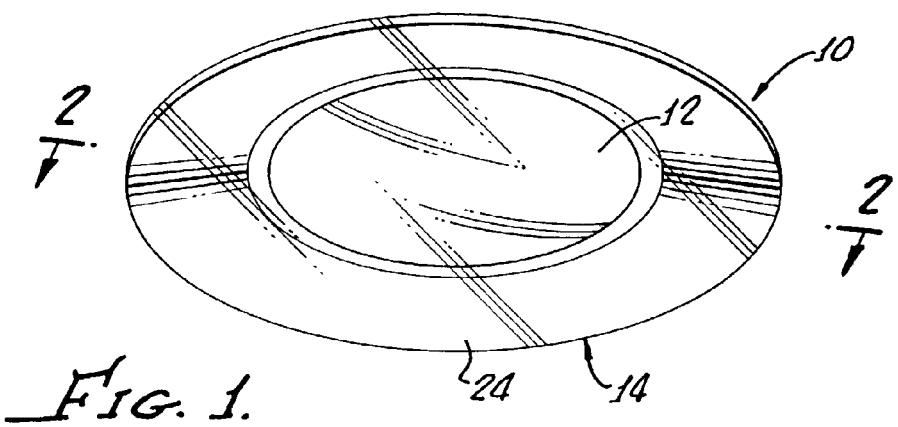
FIG. 1 is a front elevational view of an IOL assembly in accordance with another embodiment of the invention.
Figure 2:
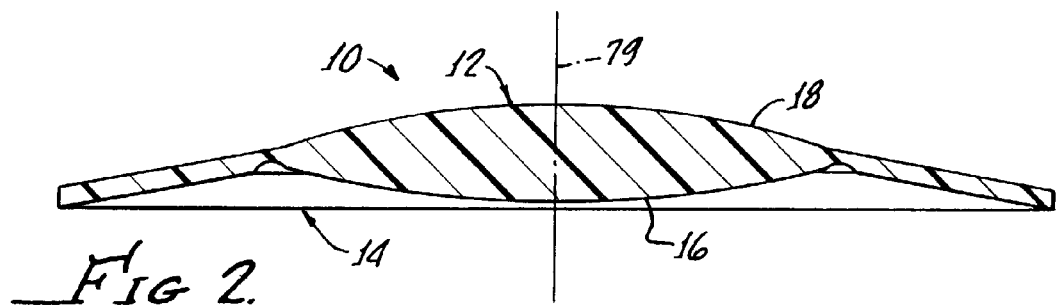
FIG. 2 is a cross-sectional view of the IOL assembly of FIG. 1.

Referring now to FIGS. 1 and 2, an intraocular lens (IOL) assembly 10 includes a lens body 12 and movement assembly 14. The lens body 12 may be constructed of rigid biocompatible materials, such as polymethyl methacrylate (PMMA), or flexible, deformable materials, such as silicone polymeric material, hydrogel polymeric material and the like, which enable the lens body 12 to be rolled or folded for insertion through a small incision into the eye.

For purposes of illustration only, the lens body 12 is shown as having a spheric convex posterior surface 16 and an aspheric convex anterior surface 18. However, the only essential feature of the lens body 12 according to this embodiment is that at least one of the surfaces is aspheric, and that both surfaces are azonal. The principles of the invention apply equally well whether it is the anterior or the posterior surface which is aspheric, and whether the surfaces are convex or concave.

For the purposes of this invention, an aspheric surface is defined as a surface of revolution having a curvature which varies continuously and monotonically from its periphery to its axis of symmetry. Ellipsoids and parabaloids are two common examples of aspheric surfaces. The anterior surface 18 of the lens 12 shown in FIG. 2 is generally elliptical, and can be described by the equation $$a^2/x^2 + b^2/y^2 = 1,$$

where a is the length of the semi-major axis, and b is the length of the semi-minor axis. Moreover, the surface 18 is a prolate ellipsoid surface. Thus, both the curvature of the surface and the refractive power of the lens increase from the optical axis to the periphery of the optical zone. However, in some cases, it may be preferable to use an oblate ellipsoid surface, in which the refractive power of the lens decreases from the optical axis to the periphery of the optical zone. The same type of lens (i.e. oblate or prolate) may be used in both eyes, or an oblate design may be used in one eye and a prolate design used in the other. Furthermore, various types of aspheric profiles other than ellipsoid can be used, such as paraboloid and more complex curvatures that can be described by higher order polynomials. In short, the specific types and combinations of aspheric surfaces used are dependent on the needs of each individual patient, and can be determined on a case-by-case basis using standard ophthalmic techniques.

Because the surface 18 is aspheric, there is no need for a plurality of discrete optical zones. In effect, the entire optical surface comprises a single zone, which typically measures from about 4 to about 7 mm across. Thus, the power of the IOL lens body 12 varies continuously and progressively from the optical axis 19 to the periphery of the lens, as shown by the simple, continuous, and monotonic curve 22 in FIG. 3, in contrast with the rather complex surface diopter distribution associated with zoned multifocal lenses. The elimination of discrete zones may reduce visual aberrations such as glare and night-time halo effects, thus making the aspheric lens 12 preferable to a multi-zoned lens for some patients. In addition, the aspheric configuration of the surface 18 may compensate for unwanted over-refractions due to errors in biometric measurements or calculations, as well as shifts in IOL position due to postoperative changes in intraocular tissue and other structures.

The illustrated movement assembly 14 comprises a flexible member 24 that circumscribes the lens body 312 and maintains the lens body 312 in an anteriorly spaced position relative to the posterior wall of the capsular bag of a patient's eye. Preferably, the flexible member 24 is integrally coupled to the lens body via a reduced thickness portion 26 that serves essentially as a hinge facilitating axial movement of the lens body 12. Further particulars of the movement assembly 14 can be found in aforementioned U.S. Pat. No. 6,406,494 to Laguette et al. These particulars are not essential, however, and any assembly effecting sufficient axial movement of the lens body 12 is within the scope of the invention.

The determination of how much axial movement is "sufficient" may of course vary from patient to patient. Preferably, however, the amount of accommodation obtained from the movement assembly should be in the range of more than about 0.5 mm, and more preferably, at least about 0.75 mm. In a very useful embodiment, the accommodation assembly should allow about 1 mm or more of axial movement. Axial movement of this magnitude has been found to increase a typical patient's accommodation by about +1 to +2 diopters.

Figure 3:
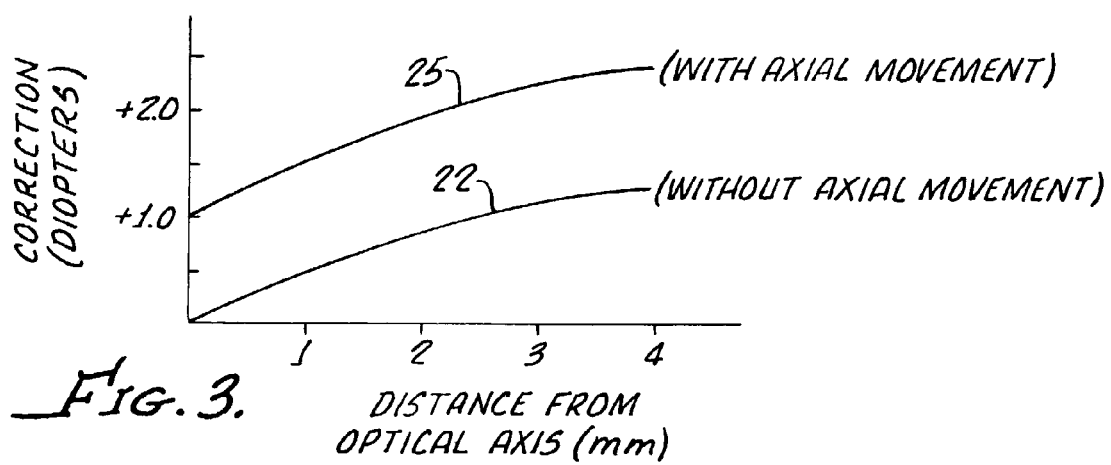
FIG. 3 is a plot of the power of the lens body of the IOL assembly shown in FIG. 1 vs. distance from the optical axis of the lens body.

The amplifying effect of the movement assembly 14 is illustrated by the curve 25 in FIG. 3. The exemplary lens body 12 has corrective powers which range from 0 diopters at the optical axis to +1.5 diopters at the periphery of the optical surface. The accommodation assembly 14 allows enough axial movement to add another +1 diopter of correction. Thus, the total amount of correction available to the patient ranges from 0 diopters, corresponding to the patient's basic distance prescription, at the optical axis when the lens body 12 is in its rearmost position to +2.5 diopters at the periphery of the lens body 12 when the lens body 12 is in its anteriormost position. Since "full add power" is approximately +2.5 diopters for the average aphakic patient, this configuration should be suitable for most individuals. However, the power variation across the optic surface can be made larger or smaller, typically anywhere in a range of +0.5 to +2.5 diopters, depending on the needs of the specific patient. Similarly, the amount of accommodation provided by the movement assembly 14 may vary from patient to patient, and is typically in the range of +1 to +2 diopters.

Figure 4:
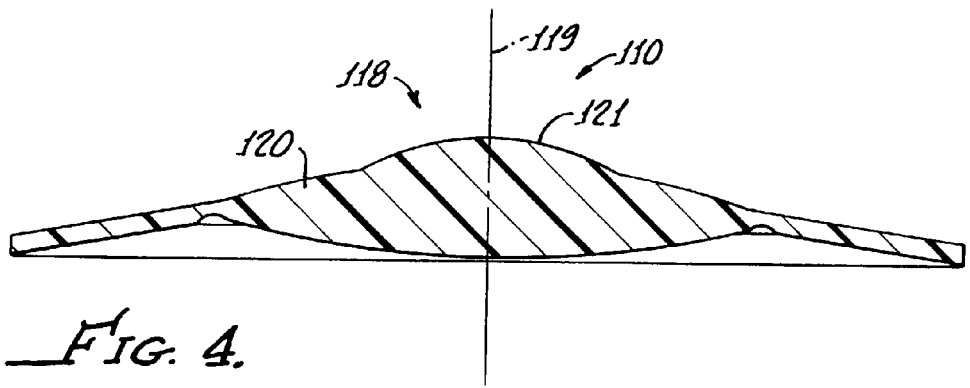
FIG. 4 is a cross-sectional view of an IOL assembly according to still another embodiment of the present invention.
Figure 5:
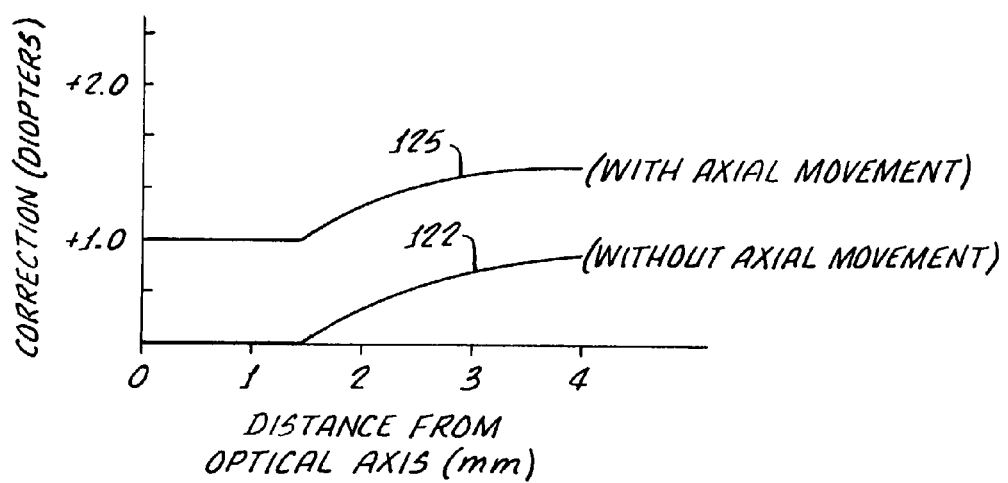
FIG. 5 is a plot of the power of the lens body of the IOL assembly shown in FIG. 10 vs. distance from the optical axis of the lens body.

FIG. 4 illustrates yet another embodiment of the IOL assembly, shown generally at 110. The IOL assembly 110 includes a convex anterior surface 118 having an aspheric peripheral portion 120 having a curvature which is generally similar to the curvature of the aspheric surface 18 of IOL assembly 110, and a spheric central portion 121. Preferably, each of these portions 120 and 121 measures from 4.0 to 7.0 mm across. The combination of a spheric portion 121 with an aspheric portion 120 serves to limit the portion of the optic with variable power. Thus, the correction provided in the center of the lens is constant, as shown by the flattened portions of the power curves 122 and 125 in FIG. 5. This type of lens may be preferable for younger patients who have some natural accommodating ability remaining in their eyes.

Alternatively, an IOL assembly may be provided with a spheric peripheral portion and an aspheric central portion, so that correction varies in the center and is constant at the periphery. In addition, the lens need not be symmetrical about the optic axis 119, That is, either the spheric portion or the aspheric portion can be located in the inferior nasal quadrant or any other suitable position in the lens. In other words, the relative size and location of the spheric and aspheric portions are not critical features of the invention and can be varied depending on the needs of the patient.

The present IOLs very effectively provide for enhanced accommodation in cooperation with the eye. Thus, the accommodating movement of the IOL, together with the multifocal characteristics of the lens body of the present IOL, provide substantially enhanced performance, for example, relative to a spheric, monofocal IOL adapted for accommodating movement or an aspheric IOL located in a substantially fixed position within the eye. The exemplary embodiments illustrated herein are presented for illustrative purposes and are not intended to be limiting to the broad scope of the present invention.

While this invention has been described with respect to various specific examples and embodiments, it is to be understood that the invention is not limited thereto and that it can be variously practiced within the scope of the following claims.

What is claimed is:

1. An intraocular lens assembly comprising:
    a lens body having an optical axis, a periphery, and an aspheric optical surface configured to provide an optical power that continuously and progressively increases from the optical axis to the periphery; and
    a movement assembly positioned relative to the lens body and configured to cooperate with the lens body to effect accommodating movement of the lens body in the eye.

2. The intraocular lens assembly according to claim 1, wherein:
    the intraocular lens assembly is configured for implantation into the eye of a presbyopic patient having a basic prescription for far vision correction and a full add power prescription for near vision correction;
    the optical surface is configured to provide variable vision correction power that varies continuously and progressively from a first diopter value corresponding to the patient's basic prescription to a second diopter value that is less than the patient's full add power prescription; and
    the movement assembly is configured to effect sufficient axial movement to provide additional add power that, when added to the second diopter value, substantially equals the patient's full add prescription.

3. The intraocular lens assembly according to claim 2, wherein the second diopter value is from about 0.5 to about 2.5 diopters greater than the first diopter value.

4. The intraocular lens assembly according to claim 1, wherein the accommodating movement is axial movement.

5. The intraocular lens assembly of claim 4, wherein the movement assembly is configured to provide at least about 0.5 mm of axial movement.

6. The intraocular lens assembly of claim 4, wherein the movement assembly is configured to provide at least about 0.75 mm of axial movement.

7. The intraocular lens assembly of claim 6, wherein the movement assembly is configured to provide at least about 1 mm of axial movement.

8. The intraocular lens assembly according to claim 1, wherein the entire optical surface has a diameter in the range of about 4.0 to about 7.0 mm.

9. The intraocular lens assembly of claim 1, wherein the movement assembly is adapted to cooperate with at least one of the ciliary muscle of the mammalian eye, the zonules of the mammalian eye and the vitreous pressure in the eye to effect accommodating movement of the lens body in the eye.

10. The intraocular lens assembly of claim 1, wherein the movement assembly comprises a flexible member circumscribing the lens body.

11. The intraocular lens assembly of claim 10, wherein:
    the lens body is configured for placement in the capsular bag of an eye; and
    the movement assembly is configured to maintain the lens body in an anteriorly spaced position relative to a posterior wall of the capsular bag.

12. The intraocular lens assembly of claim 1, wherein:
    the lens body includes an anterior surface and a posterior surface;
    one of the anterior and posterior surfaces is azonal and aspheric; and
    the other of the anterior and posterior surfaces is azonal and spheric.

13. The intraocular lens assembly of claim 1, wherein the lens body is configured to provide the lens assembly with enhanced accommodation performance relative to a spheric, monofocal lens body in combination with a substantially identical movement assembly.

14. The intraocular lens assembly of claim 1, wherein the movement assembly is configured to provide the lens assembly with enhanced accommodation performance relative to a substantially identical lens body located in a substantially fixed position in the eye.

15. The intraocular lens assembly of claim 1, wherein the optical surface is azonal and aspheric.

16. An intraocular lens assembly comprising:
a lens body having an optical axis, a periphery, an anterior surface and a posterior surface, at least one of the surfaces comprising a spherical central portion and a single aspheric optical zone configured to provide an optical power that continuously and progressively increases from a periphery of the central portion to the periphery of the lens body, the aspheric optical zone having a diameter in the range of about 4.0 to about 7.0 mm; and
a movement assembly positioned relative to the lens body and configured to cooperate with at least one of the ciliary muscle of the mammalian eye, the zonules of the mammalian eye and the vitreous pressure in the eye to effect accommodating movement of the lens body in the eye.

17. The intraocular lens assembly according to claim 16, wherein:
the intraocular lens assembly is configured for implantation into the eye of a presbyopic patient having a basic prescription for far vision correction and a full add power prescription for near vision correction;
the aspheric optical zone is configured to provide variable vision correction power that varies continuously and progressively from a first diopter value corresponding to the patient's basic prescription to a second diopter value that is less than the patient's full add power prescription; and
the movement assembly is configured to effect sufficient axial movement to provide additional add power that, when added to the second diopter value, substantially equals the patients full add prescription.

18. The intraocular lens assembly according to claim 17, wherein the second diopter value is from about 0.5 to about 2.5 diopters greater than the first diopter value.

19. The intraocular lens assembly according to claim 16, wherein the accommodating movement is axial movement.

20. The intraocular lens assembly of claim 19, wherein the movement assembly is configured to provide at least about 0.5 mm of axial movement.

21. The intraocular lens assembly of claim 19, wherein the movement assembly is configured to provide at least about 0.75 mm of axial movement.

22. The intraocular lens assembly of claim 19, wherein the movement assembly is configured to provide at least about 1 mm of axial movement.

* * * * *